US008730050B2

(12) United States Patent
Bregeon

(10) Patent No.: US 8,730,050 B2
(45) Date of Patent: May 20, 2014

(54) DEVICE FOR MONITORING THE CONDITION OF A FLUID RECEPTACLE

(75) Inventor: Frederic Bregeon, Sanit Ave (FR)

(73) Assignee: Hill-Rom SAS, Pluvigner (FR)

( * ) Notice: Subject to any disclaimer, the term of this patent is extended or adjusted under 35 U.S.C. 154(b) by 763 days.

(21) Appl. No.: 12/952,340

(22) Filed: Nov. 23, 2010

(65) Prior Publication Data
US 2011/0128152 A1 Jun. 2, 2011

(30) Foreign Application Priority Data

Nov. 30, 2009 (FR) ...................................... 09 58484

(51) Int. Cl.
G08B 21/00 (2006.01)

(52) U.S. Cl.
USPC ........... 340/603; 340/606; 340/612; 604/245; 604/246

(58) Field of Classification Search
USPC ......... 340/603, 604, 611, 612, 614, 618, 606; 604/49, 50, 245, 246, 503, 506
See application file for complete search history.

(56) References Cited

U.S. PATENT DOCUMENTS

| 4,198,626 | A |   | 4/1980  | Rauscher |
|-----------|---|---|---------|----------|
| 4,378,854 | A | * | 4/1983  | Rosen ........................... 177/118 |
| 4,650,464 | A |   | 3/1987  | Ruiz et al. |
| 4,994,026 | A | * | 2/1991  | Fecondini ........................ 604/29 |
| 5,423,781 | A | * | 6/1995  | Alexander et al. ............ 604/318 |
| 6,590,167 | B2 | * | 7/2003 | Clare .......................... 177/25.13 |
| 6,690,280 | B2 | * | 2/2004 | Citrenbaum et al. ......... 340/603 |
| 2006/0253064 | A1 | | 11/2006 | Gelfand et al. |
| 2008/0027409 | A1 | | 1/2008 | Rudko et al. |
| 2008/0204261 | A1 | | 8/2008 | Wiggins |

FOREIGN PATENT DOCUMENTS

| DE | 297 16 188 U1 | 11/1997 |
| LU | 67974 | 7/1973 |
| LU | 67 974 A1 | 9/1973 |
| WO | 2004/110525 A1 | 12/2001 |
| WO | WO 2004/110525 A1 | 12/2004 |
| WO | 2008/048482 A2 | 4/2008 |
| WO | WO 2008/048482 A2 | 4/2008 |
| WO | 2009/131266 A1 | 10/2009 |
| WO | WO 2009/131266 A1 | 10/2009 |

OTHER PUBLICATIONS

European search report from related EP 10 19 2508 dated May 3, 2011, 4 pages.

* cited by examiner

Primary Examiner — Hung T. Nguyen
(74) Attorney, Agent, or Firm — Barnes & Thornburg LLP

(57) ABSTRACT

A device for monitoring the condition of a fluid receptacle such as one that is gradually filling or emptying is disclosed. The receptacle is attached to a torque weighing device, coupled with a transducer that outputs a measurement signal representing the weight of the receptacle. An alert or alarm may be generated by a signaling device in response to the measurement signal.

20 Claims, 1 Drawing Sheet

DEVICE FOR MONITORING THE CONDITION OF A FLUID RECEPTACLE

CROSS-REFERENCE TO RELATED APPLICATIONS

The present application claims priority, under 35 U.S.C. §119(a), of French National Application No. 0958484 which was filed Nov. 30, 2009 and which is hereby incorporated by reference herein.

BACKGROUND

The present disclosure relates to a device that monitors the condition of a receptacle holding biological and medical fluids in hospitals, geriatric units or similar environments. More particularly, the present disclosure relates to monitoring the filling or emptying of a fluid receptacle that, in some instances, is in the form of a soft-sided pouch suspended from the edge of a bed frame, when acting as a fluid drainage receptacle, or from a stand, when acting as a drip bag.

It is desirable to improve the monitoring of slow processes in the hospital or geriatric environment without having to excessively multiply the number of ward rounds imposed on the nursing staff. It is therefore desirable to have a simple system that attracts attention when a fluid receptacle requires changing.

SUMMARY

A device or apparatus for monitoring the condition of a fluid receptacle is provided. The apparatus comprises one or more of the features recited in the appended claims and/or the following features which, alone or in any combination, may comprise patentable subject matter:

An apparatus may include a housing and a torque arm coupled to the housing at a pivot point located inside the housing. The torque arm may have a first end region exposed outside the housing which may be configured for coupling to the fluid receptacle. The apparatus may further include a transducer that may be located inside the housing, that may be in contact with the torque arm, and that may output a measurement signal on a substantially ongoing basis to indicate the weight of said fluid receptacle.

The apparatus may further comprising a comparator that may receive the measurement signal and compares it with a reference signal. The reference signal may adjustable in some embodiments. The apparatus may further have an alarm that is coupled to the comparator and that may be operable to emit at least one of an audible alarm and visual alarm when the measurement signal and reference signal meet a threshold condition. The threshold condition may comprise a predetermined ratio, for example. The apparatus may have a calculator to calculate whether the measurement signal meets the predetermined ratio. In some instances, the calculator may be interposed between the comparator and the alarm. The alarm may include a monitor to display the visual alarm. Alternatively or additionally, the alarm may comprise a buzzer to produce the audible alarm.

The torque arm may have a second end region that is located in the housing and that contacts the transducer. In some embodiments, the pivot point may be situated between the second end region that contacts the transducer and the first end region to which the fluid receptacle couples. The transducer may be located above the torque arm and particularly, above the second end region of the torque arm. In some embodiments, the transducer comprises a strain gage.

In some uses, the housing of the apparatus may be mounted on a bed frame and the fluid receptacle may include a collection bag for biological fluid drained from a patient. In other uses, the housing may be suspended by a stand next to a bed and the fluid receptacle may contain infusion fluid. The first end region of the torque arm may comprise a hook. The housing may comprise a box.

The apparatus may include circuitry that may be configured to receive the measurement signal output by the transducer and that may be configured to determine at least one of a fluid flow and duration of use before intervention should be made. A monitor to display a time at which the intervention should be made may be provided. For example, the monitor may be at a location remote from the housing, the torque arm, and the transducer.

According to some embodiments, therefore, the device that monitors the condition of the fluid receptacle, such as in hospitals, geriatric units or similar locations, includes a torque weighing device for said receptacle, coupled with a transducer that outputs a measurement signal representing the weight of said receptacle, calculation means controlled by said measurement signal and signaling means controlled by said calculation means.

For example, the aforementioned torque weighing device may include a simple hook lever from which the receptacle is suspended and which is mechanically coupled to a gauge comprising the aforementioned transducer.

In some embodiments, the device comprises comparison means that receives the aforementioned measurement signal along with a reference signal which, optionally, may be adjustable. The signaling means may comprise alarm means, connected to the aforementioned comparison means to emit an alarm whenever the measured signal and the reference signal reach a predetermined ratio, e.g. when they are equal.

The alarm may be an audible and/or a visual (e.g., illuminating) signal. For example, this system lends itself well to information centralization if the alarm messages are sent to a display system (e.g., TV monitor) located in a monitoring station. In this case, one person has access to all the information of this kind, covering several patients. The signaling means may also include a local or centralized buzzer.

When the receptacle is a collection pouch for biological fluid drained from a bed-bound patient, the reference signal is adjusted to indicate when the maximum filling level has been reached, thereby indicating that the collection bag should be changed.

In cases where the torque device is suspended by a stand next to the bed and where the receptacle contains an infusion fluid, the aforementioned reference signal is instead adjusted to determine when the bag is empty or almost empty.

In some embodiments, the calculation means controlled by the signal delivered by the comparator may be supplemented to determine the allowable values of the signal delivered by the transducer. For example, if the signal is measured continuously, the flow of fluid entering or leaving the receptacle can be deduced or calculated. From this flow, and knowing the maximum possible capacity or the initial capacity, it is possible to calculate the duration of use before an intervention and therefore display the time at which an intervention should be made.

In cases where the biological fluid collection bag is positioned along the frame of a height-adjustable bed, it is also helpful to be able to detect a sudden change in weight (lightening in particular) of said pouch. This may indicate that the bed height has been lowered to a point that the collection bag touches the ground, resulting in a flawed measurement. All of these applications are within reach of those capable of designing the overall measuring and signaling system, particularly the aforementioned calculation means adapted to these applications.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

A device or apparatus according to this disclosure will be better understood and its other features will become clearer after reading the following detailed description, which provides examples of the monitoring device and should be read in conjunction with the attached illustration, whereby.

DETAILED DESCRIPTION

Figure 1:
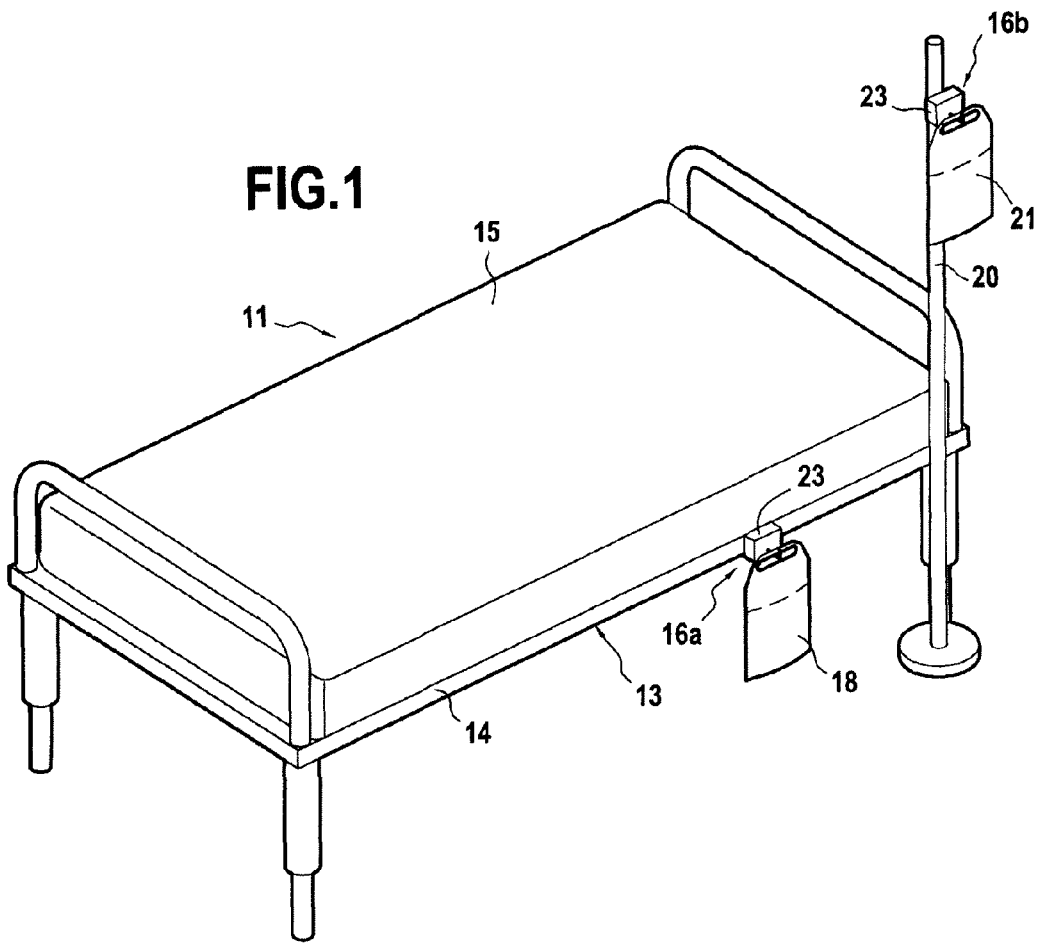
FIG. 1 is a schematic view of a hospital or geriatric unit bed, equipped, in accordance with the present disclosure, with two monitoring devices.

Referring to FIG. 1, a hospital bed 11 has a rigid metal frame 13, on top of which rests a mattress 14. The bed frame 13 is height-adjustable.

Along the edge of the bed frame 13, a first device 16a for monitoring the condition of a fluid receptacle 18, in this case a biological fluid collection bag, is provided. Near the head end of the bed 11, a stand 20 is located, at the top of which a second device 16b is provided, which, in accordance with the present disclosure, is for monitoring the condition of a receptacle 21, in this case a substantially watertight pouch containing infusion fluid.

Figure 2:
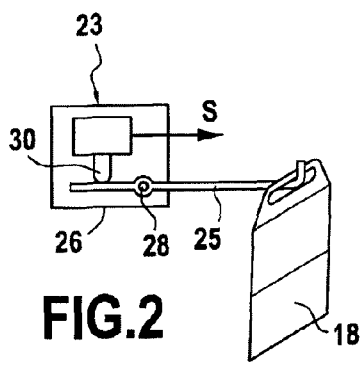
FIG. 2 is a detailed schematic view illustrating, more specifically, the torque weighing device.

FIG. 2 shows the extremely simple structure of a torque weighing device 23 for such a liquid receptacle. This receptacle 18 or 21 is suspended from the end of a torque arm or hook lever 25 which is supported by a box or housing 26 attached to the bed frame 14 or stand 20. The hook lever 25 is pivotably attached or coupled to the housing 23 at pivot point 28 and is in contact at the other end with a strain gauge 30 installed inside the box 23. This strain gauge 30 thus constitutes a transducer, delivering a measurement signal that represents or correlates to the weight of the receptacle 18, 21.

Figure 3:
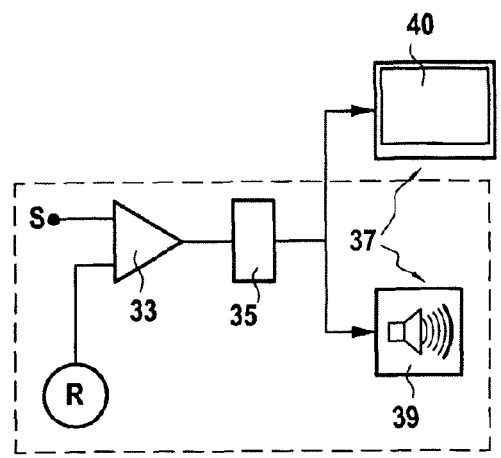
FIG. 3 is a diagram of the electronic surveillance and signaling system that receives the measurement signal delivered by the transducer coupled with the torque weighing device shown in FIG. 2.

The measured signal S delivered by the transducer 30 is processed by the system illustrated in FIG. 3. This system comprises comparison means 33, calculation means 35, which is controlled by the signal delivered by the comparison means, and signaling means 37, controlled by the aforementioned calculation means. In the illustrative example, the comparison means 33 comprises a comparator that is coupled to an audible (or illuminating) warning device 39 and a television monitor 40, which is possibly located in a remote location, which receives a video signal produced by the aforementioned calculation means 35 in order to remotely display a number of unencrypted data derived from the receptacle weighing device in a centralized monitoring station. Thus, audible warning device 39 and monitor 40 are each examples of signaling means according to this disclosure. The calculation means 35 comprises a calculator or computer or similar logic based circuitry.

The values calculated or deduced from the signal delivered by the (or each) transducer 30 are listed there above and on a nonrestrictive basis.

It is understood that, applied to the comparator input 33, the signal S is compared to a reference signal R, which, in turn, is applied to a second comparator input. This value is set by the operator such as, for example, upon attaching the receptacle to the torque weighing device. The maximum value is used for the reference signal R when the purpose of the receptacle is to collect drained fluid and the minimum value for the reference signal R is used when the receptacle contains infusion fluid and is attached to the stand.

When the S and R values are equal (or fall within a given ratio), the calculating means 35 are controlled for the processing of alarm messages and signals.

Although certain illustrative embodiments have been described in detail above, many embodiments, variations and modifications are possible that are still within the scope and spirit of this disclosure as described herein and as defined in the following claims.

The invention claimed is:

1. An apparatus for monitoring the condition of a fluid receptacle, the apparatus comprising:
   a housing,
   a torque arm pivotably coupled to the housing at a pivot point located inside the housing, the torque arm having a first end region exposed outside the housing and configured for coupling to the fluid receptacle, and
   a transducer that is located inside the housing, that is in contact with the torque arm, and that outputs a measurement signal on a substantially ongoing basis to indicate the weight of said fluid receptacle, the torque arm bearing physically against the transducer such that the measurement signal output by the transducer is continuously variable as the weight of the fluid receptacle changes.

2. The apparatus of claim 1, further comprising a comparator that receives the measurement signal and compares it with a reference signal.

3. The apparatus of claim 2, wherein the reference signal is adjustable.

4. The apparatus of claim 2, further comprising an alarm coupled to the comparator and operable to emit an audible alarm or a visual alarm or both when the measurement signal and reference signal meet a threshold condition.

5. The apparatus of claim 4, wherein the threshold condition comprises a predetermined ratio and further comprising a calculator to calculate whether the measurement signal meets the predetermined ratio.

6. The apparatus of claim 5, wherein the calculator is interposed between the comparator and the alarm.

7. The apparatus of claim 4, wherein the alarm comprises a monitor to display the visual alarm.

8. The apparatus of claim 4, wherein the alarm comprises a buzzer to produce the audible alarm.

9. The apparatus of claim 1, wherein the torque arm has a second end region that is located in the housing and the second end region contacts the transducer.

10. The apparatus of claim 9, wherein the pivot point is situated between the second end region that contacts the transducer and the first end region.

11. The apparatus of claim 9, wherein the transducer is located above the second end region of the torque arm.

12. The apparatus of claim 1, wherein the transducer is located above the torque arm.

13. The apparatus of claim 1, wherein the transducer comprises a strain gage.

14. The apparatus of claim 1, wherein the housing is mounted on a bed frame and the fluid receptacle comprises a collection bag for biological fluid drained from a patient.

15. The apparatus of claim 1, wherein the housing is suspended by a stand next to a bed and the fluid receptacle contains infusion fluid.

16. The apparatus of claim 1, further comprising circuitry configured to receive the measurement signal output by the transducer and configured to determine at least one of a fluid flow and duration of use before intervention should be made.

17. The apparatus of claim 16, further comprising a monitor to display a time at which the intervention should be made.

18. The apparatus of claim 17, wherein the monitor is at a location remote from the housing, the torque arm, and the transducer.

19. The apparatus of claim 1, wherein the first end region of the torque arm comprises a hook.

20. The apparatus of claim 1, wherein the housing comprises a box.

* * * * *